United States Patent [19]

Weston

[11] 4,190,584

[45] Feb. 26, 1980

[54] PROCESS FOR PREPARING OXAZOLES

[75] Inventor: George O. Weston, Havant, England

[73] Assignee: John Wyeth & Brother Limited, Maidenhead, England

[21] Appl. No.: 925,123

[22] Filed: Jul. 17, 1978

Related U.S. Application Data

[63] Continuation-in-part of Ser. No. 822,596, Aug. 8, 1977, abandoned.

[30] Foreign Application Priority Data

Aug. 13, 1976 [GB] United Kingdom ............... 33876/76

[51] Int. Cl.² .................... C07D 263/32; A61K 31/42
[52] U.S. Cl. ..................................... 548/236; 424/272
[58] Field of Search ................................... 260/307 R

[56] References Cited

U.S. PATENT DOCUMENTS 3,578,671  5/1971  Brown ................................. 260/307

FOREIGN PATENT DOCUMENTS 1206403  9/1970  United Kingdom .

Primary Examiner—Jose Tovar
Attorney, Agent, or Firm—Arthur E. Wilfond

[57] ABSTRACT

(4,5-Diaryloxazol-2-yl)propionic and butyric acids having anti-inflammatory activity had previously been prepared by esterification of aroylarylcarbinols with a reactive derivative of butanedioic and pentanedioic acids, for instance, succinic or glutaric anhydride, isolation of the keto ester so formed and cyclization of the keto ester with a nitrogen-donating cyclizing agent, for instance, ammonium acetate in acetic acid. It has now been found that the omission of the isolation of the keto ester intermediate improves the purity of the oxazole product.

7 Claims, No Drawings

PROCESS FOR PREPARING OXAZOLES

This application is a continuation-in-part of copending application Ser. No. 822,596, filed Aug. 8, 1977, now abandoned.

The invention relates to a method of preparation of 4,5-diaryloxazol-2-yl alkanoic acids and their salts.

(4,5-Diaryloxazol-2-yl)propionic and butyric acids and their salts are known from British Patent Specification No. 1,206,403. They exhibit pharmacological activity, particularly anti-inflammatory activity. One such anti-inflammatory agent is β-(4,5-diphenyloxazol-2-yl)propionic acid. The procedure disclosed for the preparation of this compound is as follows:

(a) Benzoin (21.2 g.) and succinic anhydride (10.0 g.) were heated together at 120° C. for 6 hours. After cooling, the glass-like solid formed was dissolved in ether, and extracted with dilute aqueous sodium carbonate solution. The basic extract was washed once with ether, and then acidified with hydrochloric acid. The resulting oil was extracted with ether and the extract washed with water, dried over $Na_2SO_4$ and evaporated to give an oil which solidified to form prismatic crystals of benzoin hemi-succinate ester 27 g., 87%), m.p. 86°-88° C. An analytical sample was recrystallised from aqueous acetone to give prisms, m.p. 88.5°-89.5° C.

(b) Benzoin hemisuccinate ester (15 g.) and ammonium acetate (30 g.) were heated in refluxing glacial acetic acid (100 ml.) for 1½ hours. After cooling, the solution was poured into water, and the resulting crystalline precipitate was filtered off, washed with water and recrystallised from methanol to give needle-like crystals of β-(4,5-Diphenyloxazol-2-yl)propionic acid (11.7 g., 83%), m.p. 160.5°-161.5° C. The overall yield amounts to 87%×83%, i.e. 72%.

The above experiment was carried out on a laboratory scale. Unpublished research has investigated performance of the process to prepare β-(4,5-diphenyloxazol-2-yl)propionic acid on a technical scale. Two disadvantages were found. Firstly the yield of oxazole obtained was much lower in the larger scale experiments. However, it was found that the technical scale yield could be maximised by modifying the reaction conditions used. In particular the use of pyridine in the ester formation step proved advantageous. In this way technical scale yields of crude β-(4,5-diphenyloxazol-2-yl)propionic acid were increased to 67%, calculated on the benzoin starting material.

The second disadvantage found was that the crude β-(4,5-diphenyloxazol-2-yl)propionic acid obtained proved difficult to purify. The crude product needed two recrystallisation steps to secure acceptably pure product. It was found that the crude product contained appreciable amounts of an impurity which was not effectively removed by methanol, the recrystallisation solvent used in the laboratory experiment. This impurity was found to be tetraphenylpyrazine. Laboratory experiments with various solvents showed that ethylene dichloride was the only efficient solvent for removing this impurity. However, when ethylene dichloride was employed as the recrystallisation solvent it was found that the recrystallised β-(4,5-diphenyloxazol-2-yl)propionic acid contained an unacceptable quantity of the solvent. For instance, a batch of recrystallised oxazole contained 0.3% ethylene dichloride. The boiling point of the solvent is 83° to 84° C. An attempt to remove the solvent by prolonged drying for 5 hours at 105° C. under a reduced pressure (640 mmHg) resulted in the solvent content falling from 0.3% to 0.23%. Even after the drying, the batch was rejected from the purity point of view because of the hepatotoxicity of ethylene dichloride. It was felt that the level of solvent impurity was unacceptably high for prolonged treatment of patients with the anti-inflammatory drug. Accordingly the ethylene dichloride could not be used as the final recrystallisation solvent. For this reason a second recrystallisation was performed with methanol as solvent and the resultant oxazole was found to be of acceptable purity. The dichloroethane recrystallisation had a yield of 91.5%, giving an overall yield of solvent-containing oxazole of 67%×91.5%, i.e. 61.3%. The second recrystallisation had a yield of 87%, giving an overall yield of pure oxazole of 61.3%×87%, namely 53%.

A technical scale experiment based upon the unpublished research will now be described:

(A) Preparation of Benzoin Hemisuccinate

A clean dry reactor of 20 gallon capacity (91 liters) was charged with pyridine (7.0 kg.) followed by dimethylformamide (35.5 kg.). With agitation, benzoin (18.80 kg.) and succinic anhydride (16.0 kg.) were added. The reactor was flushed with nitrogen. Under a continuing atmosphere of nitrogen, the mixture was heated to 90°-95° C. and maintained within this temperature range for 2 hours. The reaction mixture was cooled to 35°-40° C. After twenty minutes, the reaction mixture was tranferred gradually over 5 hours to a mixture of water (190 kg.) and hydrochloric acid of specific gravity 1.18 (28 kg.) at 55°-60° C. in a reactor of 50 gallon capacity (227 liters). The temperature was maintained at 50°-60° C. over the 5 hour period. Dimethylformamide (9.0 kg.) was used for washing through. The mixture was cooled slowly until product crystallised and then to 15° to 20° C. The mixture was stirred overnight at 15° to 20° C. The product was filtered on a ceramic filter and sucked well dry. The product was then washed with water ten times with 20 kg. each time. Ater each wash portion the product was sucked well dry. The product was then dried in a circulating air oven at 50°-60° C. for 12 to 18 hours. The yield obtained was 25.5 kg.

(B) Preparation of Crude β-(4,5-Diphenyloxazol-2-yl)Propionic Acid

A clean dry reactor of 50 gallon capacity (227 liters) was charged with glacial acetic acid (92.0 kg.). With agitation benzoin hemisuccinate (25.3 kg.) prepared as described under part A and ammonium acetate (31 kg.) were added. The reaction mixture was heated to 90°-95° C. and stirred at this temperature range for 1½ hours. Water (44.0 kg.) was carefully added to the reaction mixture and the mixture was reheated to 90°-95° C. The mixture was then transferred to another reactor of 50 gallon capacity (227 litres) through a pre-heated pressure filter. The first reactor and the filter were washed through with a mixture of glacial acetic acid (13.3 kg.) and water (6.2 kg.). The mixture in the reactor was then cooled to 10°-15° C. with agitation and the product was filtered on a ceramic filter. The product on the ceramic filter was then washed with a mixture prepared by adding glacial acetic acid (25.5 kg.) with agitation to water (12.5 kg.). The product on the filter was sucked well dry and then washed with demineralised water (10 kg.) and sucked well dry. The product was dried in a Mitchell oven at 80° C. for 16-18 hours. The yield of crude β-(4,5-diphenyloxazol-2-yl)propionic acid was 17.5 kg. (67% overall yield for parts A and B).

(C) Recrystallisation of Crude β-(4,5-Diphenyloxazol-2-yl)Propionic Acid

To ethylene dichloride (20 kg.) in a 50 gallon (227 liter) reactor there was charged crude β-(4,5-diphenyloxazol-2-yl)propionic acid (17.5 kg.) as obtained under Part B and ethylene dichloride (130 kg.) with agitation. The mixture was heated to reflux. All the solid dissolved. The solution was cooled to 75° C. and charcoal (0.50 kg.) was carefully added. The mixture was then heated to boiling and refluxed for 30 minutes. The solution was then transferred by means of pressure via a warmed pressure filter to another reactor of 50 gallon (227 liters) capacity. The first reactor and filter were washed through twice with ethylene dichloride (10 kg. each time). The mixture was cooled (gradually at first) over 1 hour with agitation to 20°-25° C. by means of cooling water on the jacket. The mixture was then cooled over 40 minutes to 0°-5° C. and stirred for 1 hour at this temperature range. The product was then filtered on a ceramic filter and sucked well dry. The product on the filter was washed with prefiltered ethylene dichloride (5 kg.) and sucked well dry. The product was dried in a Mitchell oven at 55°-60° C. for 6-8 hours. The yield of β-(4,5-diphenyloxazol-2-yl)propionic acid which still contained solvent was 16 kg. (91.5% yield for the recrystallisation), giving an overall yield of 61.3%.

The product was then recrystallised from methanol to remove the ethylene dichloride impurity to give 13.9 kg. of pure β-(4,5-diphenyloxazol-2-yl)propionic acid (87% yield for the methanol recrystallisation) giving an overall yield of 53% for the whole procedure.

References to gallons above and in Example 4 below are to British Imperial gallons. One Imperial gallon equals 1.2009 U.S. gallons.

The present invention is based upon the discovery that omission of the isolation of the ester intermediate surprisingly enhances the purity of the oxazole obtained prior to any recrystallisation. In particular the oxazole obtained is essentially free of the tetraphenylpyrazine impurity so that the recrystallisation from the toxic solvent ethylene dichloride is no longer necessary. Samples of crude β-(4,5-diphenyloxazol-2-yl)propionic acid obtained prior to any recrystallisation merely showed a number of faint trace impurities upon TLC (thin layer chromatography) investigation and only failed an acceptable specification in view of the number of impurities. An acceptably pure product was obtained by a single recrystallisation from methanol.

A second advantage of the new process is that it not only works effectively at laboratory scale but can also be scaled up to a technical scale without reduction in yield. For instance crude β-(4,5-diphenyloxazol-2-yl)propionic acid was prepared in a yield of 67% on a laboratory scale and 69.8% on a technical scale. Another advantage of the new process is that its technical scale yield of pure oxazole is higher than that when the isolation of the ester intermediate is included. For example, the technical scale yield of pure β-(4,5-diphenyloxazol-2-yl)propionic acid was 61.4% in Example 4 below, compared with 53% in the other technical scale process described above.

The invention provides a method of preparation of a 4,5-diaryloxazol-2-ylalkanoic acid having the formula

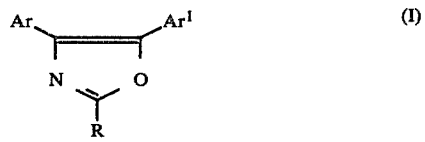

wherein Ar and $Ar^1$ represent the same or different aryl radicals and R represents carboxyethyl or carboxypropyl, or a non-toxic salt thereof, wherein an aroylarylcarbinol having the formula $$Ar-CO-CH(OH)-Ar^1 \quad (II)$$

(wherein Ar and $Ar^1$ are as defined above) is esterified with a reactive derivative of a butanedioic or pentanedioic acid to form a keto ester having the formula

(where Ar, $Ar^1$ and R are as defined above) in the reaction mixture, a nitrogen-donating cyclising agent is added to the reaction mixture and the keto ester is cyclised with the nitrogen-donating cyclising agent to form an oxazole, and, if desired, an acid product is converted into a nontoxic salt thereof.

Ar and $Ar^1$ represents the same or different aryl radicals. The term "aryl" as used herein includes heteroaryl groups, for example, thienyl or furyl. Any of the aryl groups may be substituted on the aromatic ring, but for simplicity all such aromatic radicals are referred to herein as aryl radicals. The aryl radicals contemplated include phenyl, naphthyl, thienyl and furyl radicals. Examples are unsubstituted phenyl, phenyl substituted by halogen (e.g. fluorine, chlorine, or bromine), by lower alkyl (e.g. methyl, ethyl, n-propyl, iso-propyl, n-butyl and iso-butyl), by lower alkoxy (e.g. methoxy or ethoxy), by trifluoromethyl, by nitro or by di(lower alkyl)amino (e.g. dimethylamino), or substituted or unsubstituted naphthyl, thienyl or furyl radicals (e.g. 1- or 2-naphthyl, 2- or 3-thienyl or 2- or 3-furyl). The radicals Ar and $Ar^1$ are preferably selected from unsubstituted phenyl and phenyl substituted by one or two substituents selected from halogen, lower alkyl and lower alkoxy. R represents a carboxyethyl or carboxy propyl radical, preferably carboxyethyl. The terms "lower alkyl" and "lower alkoxy" as used herein mean that the alkyl or alkoxy radical contains up to 6, preferably up to 4 carbon atoms.

The preferred esterifying agents used in the process of the invention are succinic anhydride and glutaric anhydride, advantageously succinic anhydride. We prefer to incorporate pyridine in the reaction mixture since it is advantageous as a catalyst for the ester formation and may facilitate handling at a convenient temperature. For best results we prefer to carry out the ester formation reaction under a dry inert atmosphere, e.g. nitrogen.

The cyclisation is carried out without isolation of the keto ester of formula I from the reaction mixture in which it is formed. The cyclisation is carried out directly in the said reaction mixture by adjusting the reaction mixture to the conditions used for the cyclisation step and incorporating the cyclising agent into the reaction mixture. The cyclisation works under acidic conditions and thus we prefer to add the cyclising agent in conjunction with an acid. However, the acid may be added before or after the addition of the cyclising agent. As cyclising agent there may be used urea or an ammonium salt. We prefer to use ammonium acetate as cyclising agent with acetic acid as solvent.

The invention may be carried out as follows. Succinic anhydride or glutaric anhydride and the keto alcohol are added to a suitable organic solvent such as pyridine and the mixture is heated to a temperature ranging from 90°–120° C. with stirring under a nitrogen atmosphere. The esterification may take from one to several hours. It is important that the hemisuccinate or hemiglutarate obtained as esterification product should remain in the reaction mixture before proceeding with the cyclisation step. Ammonium acetate and glacial acetic acid, preferably in the form of a solution of the ammonium acetate in the glacial acetic acid, are added to the reaction mixture and the temperature is maintained to allow the cyclisation to proceed. The cyclisation reaction may take from 1 to several hours. The product is filtered and washed with acetic acid and water to obtain the crude oxazole product. An advantage of the invention is that the crude product obtained without recrystallisation from an organic solvent may itself be of high purity.

The invention is illustrated by the following Examples:

EXAMPLE 1

A 5 liter flask was set up and equipped with stirrer, thermometer, reflux condenser and nitrogen inlet. Succinic anhydride (373 grams), benzoin (531 grams) and pyridine (300 milliliters; 296 grams) were introduced. The flask was purged with nitrogen and the reaction mixture heated to 90°–95° C. The mixture was stirred for one and a half hours at this temperature. Glacial acetic acid (1300 milliliters) and ammonium acetate (385 grams) were added to the reaction mixture and the mixture reheated to 90°–95° C. Stirring was continued and this temperature was maintained for a further 2 hours. The mixture was filtered, rinsing through with glacial acetic acid (150 milliliters). Distilled water (750 milliliters) was added and the mixture reheated to 90°–95° C. before gradual cooling with stirring to 15° C. over 1 hour. After filtering and washing with a mixture of acetic acid and distilled water in a ratio of 2:1 (600 milliliters), the product was slurried with distilled water (1000 milliliters). After filtering and washing with distilled water (2×400 milliliters), the product was dried at 90°–100° C. under vacuum. 702 Grams (67% yield) of β-(4,5-diphenyloxazol-2-yl)propionic acid were obtained as a white crystalline powder, m.p. 163°–165° C. The material was investigated for quality by TLC. The product had high purity and merely showed a number of very faint trace impurities.

EXAMPLE 2

α-(4,4-Diphenyloxazol-2-yl)butyric acid

The title compound, melting point 125°–126° C., is prepared in a similar manner to Example 1 using glutaric anhydride instead of succinic anhydride.

EXAMPLE 3

The oxazoles tabulated below are prepared from substituted benzoins indicated in a manner similar to Example 1 except that urea is used instead of ammonium acetate:

| Substituted Benzoin | Oxazole |
| --- | --- |
| Anisoin | β-[4,5-Di-(p-methoxyphenyl) oxazol-2-yl ]propionic acid, melting point 78°–82° C. |
| 2'-Chloro-3,4-dimethoxybenzoin | β-[5-(o-chlorophenyl)-4-(3',4'-dimethoxyphenyl)oxazol-2-yl] propionic acid, melting point 118°–120° C. |
| 4'-Methylbenzoin | β-[5-(4'-methylphenyl)-4-phenyl-oxazol-2-yl]propionic acid, melting point 180°–182° C. |
| 4,4'-Dichlorobenzoin | β-[4,5-(p-chlorophenyl)oxazol-2-yl]propionic acid, melting point 118°–120° C. |

EXAMPLE 4

(A) Preparation of Crude β-(4,5-Diphenyloxazol-2-yl)Propionic Acid

A clean dry reactor of 20 gallon (91 liters) capacity was charged with pyridine (9.25 kg), benzoin (16.5 kg.) and succinic anhydride (11.7 kg.). The reactor was purged with nitrogen and a nitrogen atmosphere was maintain throughout the process. The mixture was heated without agitation until it became liquid at 85° C. Agitation was commenced and the mixture was heated at 90°–95° C. for 1.5 hours. A solution of ammonium acetate (12.0 kg.) in glacial acetic acid (35.0 kg.) was charged to the header of the reactor and added to the reaction mixture over 15 minutes, maintaining the temperature between 90° and 95° C. The container for the solution and the header were washed with glacial acetic acid (4.0 kg.) and the washing liquid was added to the reaction mixture. The reaction mixture was held at 90°–95° C. for 2 hours. The reaction mixture was cooled to 50° C. and transferred via a line filter to a reactor of 50 gallon (227 liters) capacity. The first reactor, lines and filter were washed with glacial acetic acid (4.0 kg.) which was combined with the reaction mixture. The reaction mixture was heated with agitation to 90°–95° C. over 30 minutes and water (21.0 kg.) was added maintaining the temperature at 90°–95° C. The reaction mixture was then cooled to 20°–25° C. over 55 minutes by means of water in the jacket of the reactor and then cooled to 10°–15° by means of brine in the jacket and left overnight. The product was filtered on a ceramic filter and sucked well dry. The product on the filter was washed with a pre-filtered mixture of glacial acetic acid (25.5 kg.) and water (12.5 kg.) and sucked well dry. Pre-filtered water (50.0 kg.) and the filter cake were added to a reactor of 50 gallon (227 liters) capacity. The mixture was stirred at room temperature for 30 minutes and filtered on a ceramic filter and the product was sucked well dry. The product on the filter was washed twice with pre-filtered water (10 kg. each time) and sucked well dry. The product was then dried in a Mitchell oven at 80° C. for 16–18 hours. The yield of crude β-(4,5-diphenyloxazol-2-yl)propionic acid was 15.9 kg. (69.8%). This material only just failed specification for acceptable purity because although TLC analysis showed only very faint trace impurities, their number was considered excessive.

(B) Recrystallisation of Crude β-(4,5-Diphenyloxazol-2-yl)Propionic Acid

Methanol (62.0 kg.) was added to a reactor of 50 gallon capacity (227 liters). 15.9 kg. of the crude oxazole prepared in part (A) was added with agitation. The mixture was heated to reflux. All the solid dissolved. The mixture was then cooled to 50° C. and transferred to a reactor of 20 gallon (91 liters) capacity. The larger reactor and transfer lines were washed through with methanol at about 40° C. twice (3 kg. each time). The mixture was cooled over 1 hour 50 minutes with agitation, gradually at first, to 15°–20° C. by means of cooling water on the jacket of the reactor. The product was then filtered on a ceramic filter and sucked well dry. The product on the filter was washed twice with methanol (5 kg. each time) and sucked well dry. The wash liquors were combined with the filtration liquors and retained. The product from the filter was dried in an air oven at 55°–60° C. for 18 hours. The yield of β-(4,5-diphenyloxazol-2-yl)propionic acid was 12.1 kg. TLC investigation showed the product to be pure.

Another crop of product was obtained from the methanol liquors as follows. The liquors were added to a reactor of 20 gallon (91 liters) capacity and the solvent was distilled off for 9 hours until solid appeared. The mixture was then cooled to 15° to 20° C. over 1 ¾ hours using cooling water in the jacket of the reactor. The mixture was cooled to 10° C. using brine in the jacket and stirred at this temperature for 30 minutes. The product was then filtered on a ceramic filter and sucked well dry. The product on the filter was washed twice with methanol (5 kg. each time) and sucked well dry. The product was dried in an air oven at 55°–60° C. for 18 hours. The yield was 2.14 kg. This product may also have been acceptably pure but its purity was not investigated. It was therefore retained as crude product to be resubjected to recrystallisation with methanol.

The yield for the recrystallisation was thus 12.1 kg. from a consumption of 13.76 kg. of crude product, that is 88%. The overall yield of pure product is 69.8%×88%, that is, 61.4%.

I claim:

1. In a process for the preparation of a compound selected from 4,5-diaryloxazol-2-ylalkanoic acids having the formula

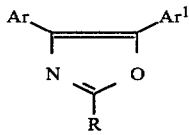

wherein Ar and Ar¹ represent the same or different aryl radicals selected from the group consisting of phenyl, naphthyl, thienyl, furyl and phenyl substituted by halogen, lower alkyl, lower alkoxy, trifluoromethyl, nitro and di(lower alkyl)amino and R represents carboxyethyl or carboxypropyl, and their non-toxic salts, wherein an aroylaryl carbinol having the formula $$Ar-CO-CH(OH)-Ar^1 \quad (II)$$

(where Ar and Ar¹ are as defined above) is esterified with a reactive derivative of a butanedioic or pentanedioic acid to form a keto ester having the formula

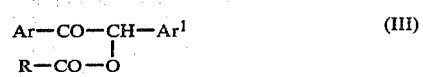

(where Ar, Ar¹ and R are as defined above) in a reaction mixture, and the keto ester is cyclised with a nitrogen-donating cyclising agent to form an oxazole, the improvement which comprises adding the nitrogen-containing cyclising agent to the reaction mixture in which the keto ester is formed.

2. In a process for the preparation of a compound selected from 4,5-diaryloxazol-2-ylalkanoic acids having the formula

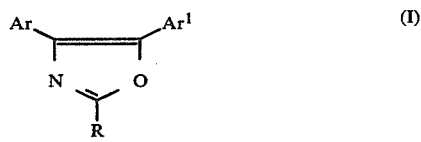

wherein Ar and Ar¹ represent the same or different aryl radicals selected from the group consisting of phenyl and phenyl substituted by one to two substituents selected from halogen, lower alkyl and lower alkoxy and R represents carboxyethyl or carboxypropyl, and their non-toxic salts, wherein an aroylaryl carbinol having the formula $$Ar-CO-CH(OH)-Ar^1 \quad (II)$$

(where Ar and Ar¹ are as defined above) is esterified with a reactive derivative of a butanedioic or pentanedioic acid to form a keto ester having the formula

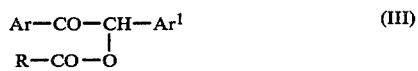

(where Ar, Ar¹ and R are as defined above) in a reaction mixture, and the said keto ester is cyclised with a nitrogen-donating cyclising agent to form an oxazole, the improvement which comprises adding the nitrogen-containing cyclising agent to the reaction mixture in which the keto ester is formed.

3. A process as defined in claim 2, wherein Ar and Ar¹ are both phenyl and R is carboxyethyl.

4. A process as defined in claim 2, wherein the said reactive derivative is succinic anhydride or glutaric anhydride.

5. A process as defined in claim 4, wherein the said nitrogen-donating cyclising agent is ammonium acetate or urea.

6. A process as defined in claim 2, wherein Ar and Ar¹ are both phenyl and R is carboxyethyl, the reactive derivative is succinic anhydride or glutaric anhydride and the nitrogen-donating cyclising agent is ammonium acetate or urea.

7. A process as defined in claim 2, wherein Ar and Ar¹ are both phenyl and R is carboxyethyl, the reactive derivative is succinic anhydride or glutaric anhydride and the nitrogen-donating cyclising agent is ammonium acetate or urea and the reaction is carried out in the presence of pyridine.

* * * * *

UNITED STATES PATENT AND TRADEMARK OFFICE

CERTIFICATE EXTENDING PATENT TERM
UNDER 35 U.S.C. § 156

PATENT NO.: 4,190,584

DATED: February 26, 1980

INVENTOR: George O. Weston

PATENT OWNER: John Wyeth & Brother Limited

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of

2 YEARS with all rights pertaining thereto as provided by 35 U.S.C. § 156(b).

I have caused the seal of the Patent and Trademark Office to be affixed this 20th day of September 1994.

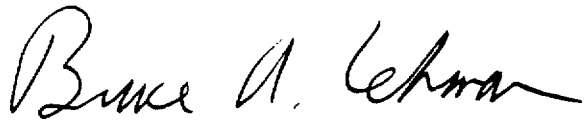

Bruce A. Lehman
Assistant Secretary of Commerce and
Commissioner of Patents and Trademarks